(12) United States Patent
Nisch et al.

(10) Patent No.: US 6,984,297 B2
(45) Date of Patent: Jan. 10, 2006

(54) DEVICE FOR TAKING MEASUREMENTS OF CELLS WHICH ARE CONTAINED IN A LIQUID ENVIRONMENT

(75) Inventors: Wilfried Nisch, Tübingen (DE); Martin Stelzle, Reutlingen (DE); Alfred Stett, Reutlingen (DE); Thomas Krahn, Hagen (DE); Thomas Müller, Bonn-Beuel (DE); Christoph Methfessel, Wuppertal (DE)

(73) Assignees: NMI Naturwissenschaftliches und Medizinisches Institut an der Universität Tübingen, Reutlingen (DE); Bayer AG, Leverkusen (DE)

( * ) Notice: Subject to any disclaimer, the term of this patent is extended or adjusted under 35 U.S.C. 154(b) by 71 days.

(21) Appl. No.: 10/302,163

(22) Filed: Nov. 20, 2002

(65) Prior Publication Data

US 2003/0080314 A1 May 1, 2003

Related U.S. Application Data

(63) Continuation of application No. 10/110,258, filed as application No. PCT/EP00/08895 on Sep. 12, 2000, now abandoned.

(30) Foreign Application Priority Data

Oct. 8, 1999 (DE) ................................ 199 48 473

(51) Int. Cl.
 C12N 9/00 (2006.01)
 C25B 11/08 (2006.01)
 C12Q 1/02 (2006.01)
 C12M 1/40 (2006.01)
 A61B 5/04 (2006.01)

(52) U.S. Cl. .................. 204/403.01; 204/643; 435/29; 435/285.1; 435/287.1; 435/288.7; 435/289.1; 600/372; 600/373

(58) Field of Classification Search ........... 204/403.01, 204/643; 435/29, 285.1, 287.1, 288.7, 289.1; 600/372, 373

See application file for complete search history.

(56) References Cited

U.S. PATENT DOCUMENTS

| 5,262,128 | A | 11/1993 | Leighton et al. |
| 5,489,515 | A | 2/1996 | Hatschek et al. |
| 6,315,940 | B1 * | 11/2001 | Nisch et al. ............. 435/287.1 |

FOREIGN PATENT DOCUMENTS

| DE | 196 46 505 A1 | 5/1998 |
| DE | 197 12 309 A1 | 5/1998 |
| DE | 198 41 337 C1 | 9/1999 |
| DE | 198 27957 A1 | 12/1999 |
| EP | 0 627 621 A1 | 12/1993 |
| EP | 0 689 051 A2 | 12/1995 |
| WO | WO 97/05922 | 2/1997 |
| WO | WO 01/25769 | 4/2001 |

* cited by examiner

Primary Examiner—David M. Naff
Assistant Examiner—Kailash C. Srivastava
(74) Attorney, Agent, or Firm—Knobbe, Martens, Olson & Bear LLP (57) ABSTRACT

A method and a device are used for carrying out measurements on cells located in a liquid environment. Each cell is positioned with an underside of its membrane on a surface having a channel running through it. A negative pressure is established to aspirate the cells. Each cell is electrically scanned via at least one electrode which is spaced apart from the cell. The negative pressure is preferably established in a pulse-like manner to rupture the membrane in such a way that the cell interior enclosed by the membrane is connected to the channel.

24 Claims, 7 Drawing Sheets

DEVICE FOR TAKING MEASUREMENTS OF CELLS WHICH ARE CONTAINED IN A LIQUID ENVIRONMENT

RELATED APPLICATION

This application is a continuation of U.S. patent application Ser. No. 10/110258, now abandoned which represents the U.S. National Stage under 35 U.S.C. 371 of International Application No. PCT/EP00/08895, which was published in a language other than English and entered the U.S. National Phase on Apr. 8, 2002, filed Sep. 12, 2000.

CROSS-REFERENCES TO RELATED APPLICATIONS

This application is a continuation of copending international patent application PCT/EP00/08895 filed on Sep. 12, 2000 designating the U.S., which claims priority of German patent application DE 199 48 473.2 filed on Oct. 8, 1999.

BACKGROUND OF THE INVENTION

The invention relates to a method for carrying out measurements on cells located in a liquid environment wherein each cell is positioned with an underside of its membrane on a surface, the surface having at least one channel running through it, in which, to aspirate the cell to the surface, a pressure differential is established and the cell, in addition, is electrically scanned via at least one electrode.

The invention further relates to a device for carrying out electrical measurements on cells located in a liquid environment, comprising a substrate which has a channel running through it, above which a cell can be positioned with an underside of its membrane on a surface of the substrate, means being provided to generate a pressure differential along the channel, and a first electrode being provided for electrical scanning of the cell.

It is known to employ so-called microelectrode arrays for the study of biological cells, the microelectrode arrays being used e.g. to stimulate the cells or to tap potentials. The studies can be carried out in a biological environment or alternatively in an artificial environment. The arrays to this end comprise, in a matrix, a plurality of microelectrodes whose dimensions are of about the order of magnitude of the cells, i.e. in a range from a few μm up to a few tens of μm. A microelectrode array of this general type is disclosed e.g. by WO 97/05922.

In conventional microelectrode arrays it is more or less a matter of having to rely on chance as to whether one cell or some other cell will or will not settle on a specific electrode. In practice, the cells will generally only partially cover an electrode when settling on it, so that stimulation of the cell or tapping of a cell potential is limited to this sub-area. Moreover, the cells are only loosely seated on the electrodes. This may lead to problems with regard to the sealing resistance with respect to the reference electrode. Alternatively, cells may come to lie outside the range of an electrode, so that the measurement will not pick them up.

In the case of the microelectrode array disclosed by DE 197 12 309 A1 these drawbacks are avoided by the cells being collected in micro-cuvettes at whose bottom an electrode is located. The electrode is provided with a central channel in which a negative pressure can be produced via suitable connecting channels which run below the electrodes. Thus it is possible for individual cells to be drawn to the electrodes in a controlled manner and to be affixed to the electrodes with a certain contact pressure. Measurements can then be carried out on the electrodes, but only from outside them.

From another art, the so-called Patch Clamp technique, it is known to aspirate cells at a pipette using negative pressure (cf. US-Z "NATURE", vol. 260, pp. 799–801, 1976). The Patch Clamp technique, however, requires a controlled approach of the pipette to an individual cell. With the Patch Clamp technique the cells to be contacted are not moved, since as a rule they are adhering to a substrate. Conventional contacting of cells using Patch Clamp pipettes has a drawback, however, that the number of cells that can be contacted simultaneously is extremely limited, since for reasons of space it is not possible to introduce arbitrarily many pipettes into the culture chamber.

On the other hand, the Patch Clamp technique has the advantage, compared with the above-described technique which only permits measurements from the outside of the cell, that the cell interior can be included in the measurement.

In the Patch Clamp technique as employed conventionally, using individual pipettes, this is achieved, under observation by microscope, by a fragile glass pipette being moved, by means of a micromanipulator, to a single cell adhering to a substrate and the membrane being cautiously aspirated to the pipette mouth. There is therefore direct contact between glass surface and membrane surface. By this means, a membrane patch is sealed and electrically insulated from the surrounding fluid. This insulation is also referred to as a gigaseal. The transition from this "cell-attached configuration" to the so-called "whole cell configuration" is achieved by further aspiration of the sealed membrane. This is done in such a way that the membrane section below the pipette is perforated. This results in hydraulically and electrically sealed access via the pipette mouth to the cell interior. The remaining cell membrane is thus electrically accessible in its entirety (so-called "whole cell patch"). Using this conventional technique does, however, require a considerable level of experience and very sensitive touch. A plurality of cells can only be processed sequentially. This method is therefore unsuitable for large-scale studies as would be required e.g. in the field of pharmaceutical screening, substance screening and the like.

SUMMARY OF THE INVENTION

It is an object of the invention to refine a method and a device of the type mentioned at the outset so as to avoid the above-mentioned drawbacks. In particular, the invention is to permit measurements as consistent as possible, preferably in parallel on a plurality of cells, and particularly as desired in the field of experimental or application-oriented screening of the action of pharmaceutical active ingredients on a cellular level.

With a method of the type mentioned at the outset this object might be achieved by the underside of the membrane being ruptured by means of an increase in the pressure differential and/or the membrane being rendered microporous and electrically low-resistant or being ruptured by means of an addition of pore-forming substances or by means of an electric current pulse.

With a device of the type mentioned at the outset, the object of the invention is achieved by at least one second electrode being arranged so as to be spaced apart, towards the channel, from the first electrode.

The object of the invention is thus completely achieved.

The invention makes it possible, compared with conventional Patch Clamp techniques, to dispense with the awkward handling of a fragile glass pipette, since the function of the conventional glass pipette is performed by the channel in a substrate, a negative pressure being applied to the channel to establish a cell-attached configuration. If a gigaseal has thus been established between the cell wall and the surface to which the cell is aspirated, according to the invention either the underside of the membrane is ruptured by an increase in the negative pressure, thus then permitting measurements to be carried out via the channel throughout the cell interior enclosed by the membrane. Alternatively, or in addition, the membrane, by means of an addition of pore-forming substances can be rendered microporous and electrically low-resistant. As a result of the addition of such pore-forming substances such as e.g. nystatine or amphotericine B, pores are formed in the membrane, thus enabling low-resistance access to the cell interior without, however, larger molecules being able to diffuse through said access. The resulting membrane currents can thus be measured without the underside of the membrane having to be destroyed for this purpose. Alternatively, the membrane in this region can also be rendered permeable or ruptured by a brief electric pulse.

A particular advantage of the invention is that the measuring electrode can be arranged spaced apart from the membrane, so that the cell does not, with its membrane, lie directly on the electrode, but the measurement is instead effected via the intracellular medium.

Whereas the known array according to DE 197 12 309 A1 only permits extracellular measurements, i.e. measurements of changes in potential, caused by membrane currents, in the immediate vicinity of the cell, the invention allows intracellular and extracellular measurements to be carried out, i.e. the voltage obtaining across the membrane can be measured and checked. This purpose is preferentially achieved by a current being injected into the membrane.

The invention is therefore especially suitable for large-scale studies in the field of pharmaceutical screening and substance screening, the identification of clones (GMOs; genetically modified organisms) and within the context of substance optimizations, where the cytoplasm of biological cells is measured electrically, either simultaneously or directly sequentially for a plurality of such cells. The invention therefore provides for the first time the option of employing a technique having the same advantages as conventional Patch Clamp techniques in a fully automated mode. It is therefore possible to study many such cells in parallel, in a manner lending itself to automation and with high throughput.

In a preferred refinement of the invention, the pressure differential to rupture the membrane is increased in a pulse-like manner.

This measure permits a controlled transition from the cell-attached configuration to the whole cell configuration.

In principle it is possible for a plurality of channels to be provided in a common substrate and, with the aid of the negative pressure, to aspirate cells to the surface of the substrate at the mouths of the channels.

According to a preferred refinement of the invention, however, the cell is positioned on the bottom of a micro-cuvette.

This measure has the advantage that a liquid medium containing the cells to be studied can be introduced in a controlled manner above each channel by means of a pipette or the like. Thus a large number of micro-cuvettes located in a common mount can be measured simultaneously via one channel each associated with a micro-cuvette and at least one measuring electrode each.

A method is preferred which involves the use, as a measurand of the electric signal, of the current ($I_{sr}$) through the cell interior of the cell and/or a measurement of the electrical potential at the electrodes.

In a preferred embodiment of the method according to the invention, the cell is electrically scanned via an electrode which is spaced apart from the underside of the membrane in the direction of the channel. A current can be injected into the cell interior for this purpose.

This measure has the advantage that direct electrical access is established only into the interior of the cell. As a result of the cell with its outer membrane being seated tightly on the bottom of the micro-cuvette and even being fixed in position there by means of negative pressure, the gigaseal, i.e. an extremely high leakage resistance, which consequently does not significantly affect the measurement, between intracellular and extracellular medium, known from the conventional Patch Clamp technique is established in an automated manner. Having the electrode spaced apart from the gigaseal further ensures that the cell itself will only come into contact with electrically insulating materials, thus ensuring that the gigaseal is maintained.

A further preferred embodiment of the method according to the invention involves, in an arrangement comprising a plurality of channels, the pressure pulse or the electric current pulse being generated simultaneously at all the channels. Alternatively, however, the pressure pulses or current pulses can be applied successively to individual selected channels, either in a sequence chosen at will or in a strictly sequential procedure.

These measures have the advantage that almost any experiments can be carried out in an automated manner on a plurality of cells, thereby producing very many measurement results per unit time.

In a preferred refinement of the method according to the invention, the composition of the intracellular liquid medium is altered by the addition of substances or the intracellular liquid medium is replaced after the membrane has been opened up or micropores have been generated. To this end, the channel can be connected to two or more connecting channels, one of which is charged with electrolyte which has a composition similar to that of the cytoplasm (intracellular fluid) or is a special fluid with added active ingredients.

This allows specific and controlled modification of the intracellular medium while at the same time considerably broadening the possible spectrum of feasible measurements.

In the device according to the invention at least one second electrode is arranged so as to be spaced apart, towards the channel, from the first electrode.

In a preferred refinement, means for controlling the pressure differential are provided, both for the purpose of generating a static pressure differential to establish a cell-attached configuration and for the purpose of a pulse-type increase in the pressure differential to rupture the underside of the membrane.

Thus it is possible, firstly, to establish the gigaseal in a reliable and controlled manner and, secondly, to maintain the gigaseal while the underside of the membrane is ruptured by a brief pressure pulse and comes to lie against the channel wall.

The control system in this context is preferably designed so as to continuously maintain the static negative pressure (offset pressure), thus maintaining the gigaseal even in the whole-attached configuration.

According to a further embodiment of the device according to the invention, the electrode is disposed on that side of the channel which faces away from the first electrode.

In this arrangement, the electrode can annularly surround the far end of the channel.

These measures have the advantage that the electrode can be integrated into a microstructure in a simple manner by being fashioned on the underside of the layer which has the channel running through it.

In a further variant of the invention, however, the electrode is spaced apart from the far end of the channel.

This provision has the advantage that the electrode, as will be explained later, can also be disposed so as to be movable relative to the channel, so that the same electrode can be used to perform measurements successively on a plurality of cells.

According to a further feature of the invention, the channel, at its end facing away from the first electrode, is connected via valves to a plurality of channels via which the fluid can be supplied or discharged.

This provision has the advantage that as a result of the pressure conditions in the connecting channels being suitably controlled, the cell interior, once the whole cell configuration has been established, i.e. once the membrane has been ruptured, will come into contact with intracellular fluid.

In an additional refinement of the invention, above the substrate a micro-cuvette is disposed in whose bottom an opening is provided.

This allows the fluid to be stored above the substrate in which in a manner particularly suitable for large-scale screening the channel or channels are provided. In such an arrangement the cells, by virtue of a suitable funnel-like design of the microcuvettes, can be guided into the immediate vicinity of a channel mouth of a substrate surface. Alternatively, however, the opening in the bottom of the micro-cuvette may have a distinctly larger diameter, thus essentially ensuring that the applied negative pressure will guide the cell as far as the mouth of the channel. This facilitates fabrication of the structure according to the invention.

In addition it is preferable for a plurality of channels to be arranged in a common substrate.

This allows compact design to be achieved in conjunction with simple fabrication.

In addition it is preferable in this context for a plurality of micro-cuvettes to be arranged in a plate.

This provides the advantage of allowing preparations to be made in a simple manner for parallel or sequential measurements on many cells, since all the micro-cuvettes are located in a common plate.

In the case of embodiments of the invention which use a common plate for the micro-cuvettes it is further preferable for the plate to have a multilayer structure.

This measure has the advantage that the different requirements with respect to the various elements of the plate can be taken into account by a suitable choice of materials.

This is particularly the case where, in a refinement of this variant, the plate comprises a top layer, a middle layer and a bottom layer, the micro-cuvettes being disposed in the top layer, the middle layer forming the substrate with the channels, and the bottom layer having disposed therein connecting channels which lead to the channels and, in a preferred embodiment, electric leads running to the channels, and microelectrodes.

This tripartite division of the plate has the advantage that the three essential functions can each be served by individual layers of different thickness and different materials being used.

According to a further embodiment of the invention, the substrate is bonded to a bottom layer which comprises one or more layers of photopatternable materials which permit spatial routing of connecting channels which run to the channels.

In such an arrangement, the bottom layer can be applied to a glass mount.

These measures allow a particularly compact design and simple fabrication. Known photopatternable materials include certain polymers, but also certain glasses.

It is preferable for the connecting channels to have a width of between 10 $\mu$m and 40 $\mu$m, preferably about 20 $\mu$m.

The channels themselves preferably have an inner width of less than 10 $\mu$m, preferably less than 5 $\mu$m.

These dimensions have proved optimal in the present context. In particular, an inner width of the channels which is smaller than the cell diameter promotes positioning of one cell at a time on a channel.

As indicated previously, it is particularly preferable in these embodiments of the invention for the electrodes to be disposed on the underside of the middle layer or the topside of the bottom layer.

This measure has the advantage that the electrodes together with their leads can be formed by simple printing, deposition, vapour deposition and subsequent mircropatterning by known methods (photolithography, etching procedures, lift-off etc.).

In this case it is further preferable for the electrodes, as seen in a plan view from above, to be fashioned as a square area having an edge length of between 20 $\mu$m and 60 $\mu$m, preferably about 40 $\mu$m.

As mentioned above, provision can be made in this case for the conductor tracks leading to the electrodes to be disposed between the middle and the bottom layer. This can be effected either by applying them to the bottom of the middle layer or to the top of the bottom layer. Application to the underside of the middle layer has the advantage that the conductor tracks can be formed together with the electrodes, especially also using the same material, particularly precious metal, preferably gold.

In this arrangement the conductor tracks preferably have a width of between 5 $\mu$m and 30 $\mu$m, particularly about 10 $\mu$m.

As mentioned above it is possible, in the case of a multilayer construction of the plate, to use different materials for the individual layers.

The various layers can be produced e.g., independently of one another from plastic, polymethylmethacrylate (PMMA), silicone, PTFE, polyimide or of an inorganic material, particularly of glass, ceramic material or silicon.

The preferred material used for the substrate is polyimide, which for this purpose is employed as a sheet in which the channels are fashioned as drilled holes. The substrate (the sheet) then preferably has a thickness of between 2 $\mu$m and 40 $\mu$m, preferably about 5 $\mu$m.

The preferred material used for the bottom layer is glass. In the glass, which can be provided in virtually any thickness, so as also to ensure the mechanical stability, the necessary connecting channels and the like can be produced in a conventional manner.

In an additional refinement of the invention it is preferable for the substrate to be disposed at the underside of a plate in which a plurality of drilled holes are fashioned as microcuvettes in whose bottom holes are provided by means of which the channels of the substrate are centred.

Thus a combined body having a plurality of micro-cuvettes to which individual channels and electrodes are allocated can be prepared in a relatively simple manner.

According to a further embodiment of the invention, a hydraulic and measuring unit is provided which has a chamber which is open towards the underside of the substrate and can be positioned at the underside of the substrate in such a way that the chamber communicates with a selected channel and is sealed with respect to the outside, the chamber containing at least one electrode and being connectable to at least one terminal channel which is connected to a negative-pressure source.

In addition, a traversing unit for traversing and positioning the plate and the negative-pressure and measuring unit relative to one another can be provided.

Thus a single measuring unit can be used for sequential measurements on a plurality of cells, which can result in considerable cost savings.

For this purpose, by preference, commercial, conventional standard grid plates (so-called "96-well plates", "384-well plates" or the like) can be used. These merely require sealing at the bottom by applying the sheet provided with channels (holes). The measurements on the many individual cells in the drilled holes of the well plate are then carried out sequentially by traversing the negative-pressure and measuring unit or conversely by traversing the standard grid plates relative to a stationary negative-pressure and measuring unit. The latter generates the negative-pressure pulse to open up the cell and also contains the electrode to carry out the subsequent measurement through the cell interior.

In so doing it is again possible, as already mentioned above, for the chamber to be connected to a plurality of terminal channels via valves, so that the cell interior is brought into contact with intracellular fluid after the whole-cell configuration has been established or that the composition of the intracellular fluid can be altered.

Further advantages can be deduced from the description and the accompanying drawing.

It goes without saying that the above mentioned features and those still to be explained hereinafter can be used not only in the combination specified in each instance, but also in other combinations or on their own without going beyond this scope of the present invention.

BRIEF DESCRIPTION OF THE DRAWINGS

Exemplary embodiments of the invention are shown in the drawing and are explained in more detail in the following description. In the drawing:

FIG. 7a) to 7c) show various phases as a cell is aspirated, a cell-attached configuration and a whole-cell configuration are established when two connecting channels to the channel are used, in a simplified, schematic view.

DETAILED DESCRIPTION OF PREFERRED EMBODIMENTS

EXAMPLE 1

In FIGS. 1 to 4, 10 denotes a plate. Established in a surface 11 of the plate 10 by means of moulding is a grid of micro-cuvettes 12. The micro-cuvettes 12 are three-dimensional and have suitable dimensions for culturing cells. A plate 10 may e.g. contain 8×12=96 micro-cuvettes 12 disposed therein.

Figure 1:
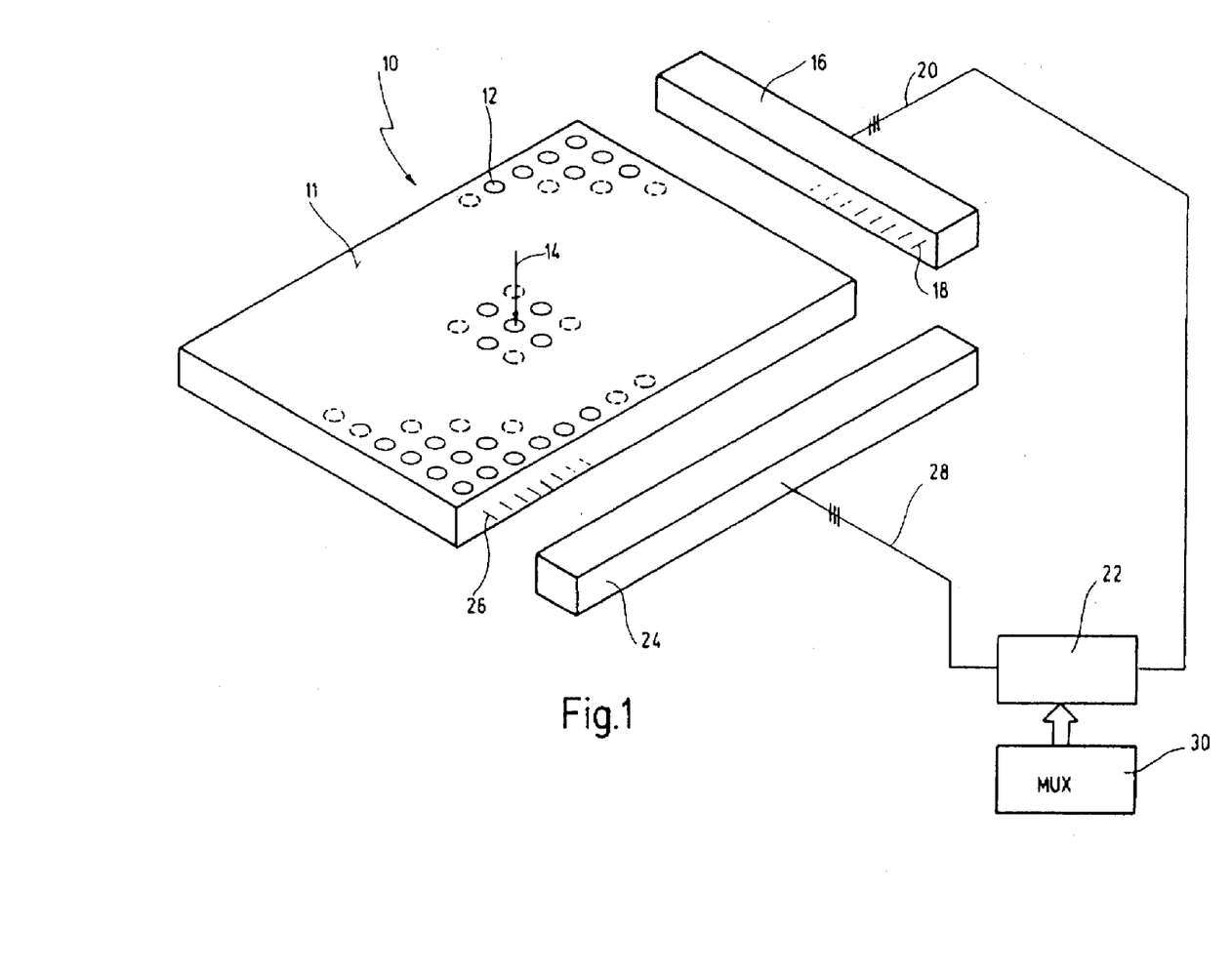
FIG. 1 shows an extremely schematic perspective view of a specific embodiment of a device according to the invention.

An arrow 14 indicates that the micro-cuvettes 12 can be charged from above, specifically with a fluid which contains cells to be studied. In so doing it is possible to charge each of the micro-cuvettes 12 individually with different fluids and cells.

For the purpose of performing the measurements, an electric terminal module 16 is provided which can be docked laterally onto the plate 10, a sufficient plurality of plugs 18 being provided for this purpose. The plugs 18 communicate with a network of conductor tracks. These conductor tracks run to electrodes which are disposed in the vicinity of the micro-cuvettes 12, as will be explained later. Running from the electric terminal module is a data line 20 to a controller 22.

Also provided is a hydraulic terminal module 24 which can like-wise be docked laterally onto the plate 10, by means of a corresponding plurality of hydraulic plugs 26. Using the hydraulic terminal module 24 it is possible, in a predetermined manner, particularly individually, to generate a negative pressure below the micro-cuvettes 12, especially as a pulse-shaped function of time, as will be explained below in detail.

To this end, the hydraulic plugs 26 are connected to the micro-cuvettes 12 via a network of connecting channels and openings 49 at the bottom of the micro-cuvettes. If the same negative pressure is to be applied to all the micro-cuvettes 12, all the connecting channels are connected in parallel and are directly linked, in the hydraulic terminal module 24, to a central, controlled negative-pressure source. If, however, the individual micro-cuvettes 12 are each to be driven with an individual negative pressure, it is likewise possible to employ a central negative-pressure source which is connected to the network of connecting channels, said connecting channels then containing individually controllable valves. Alternatively, however, it is also possible for the connecting channels to be fitted with miniaturized pumps, especially miniature membrane pumps, which are driven individually. Electric actuation of the valves and/or miniature pumps can be effected either via the electric terminal module 16 or the hydraulic terminal module 24. In each case, a line 28 for driving the abovementioned elements runs from the hydraulic terminal module 24 to the controller 22.

The controller 22 in turn communicates with a multiplexer 30 to be able to carry out, in a predetermined manner, a plurality of measurements simultaneously or optionally sequentially.

Figure 2:
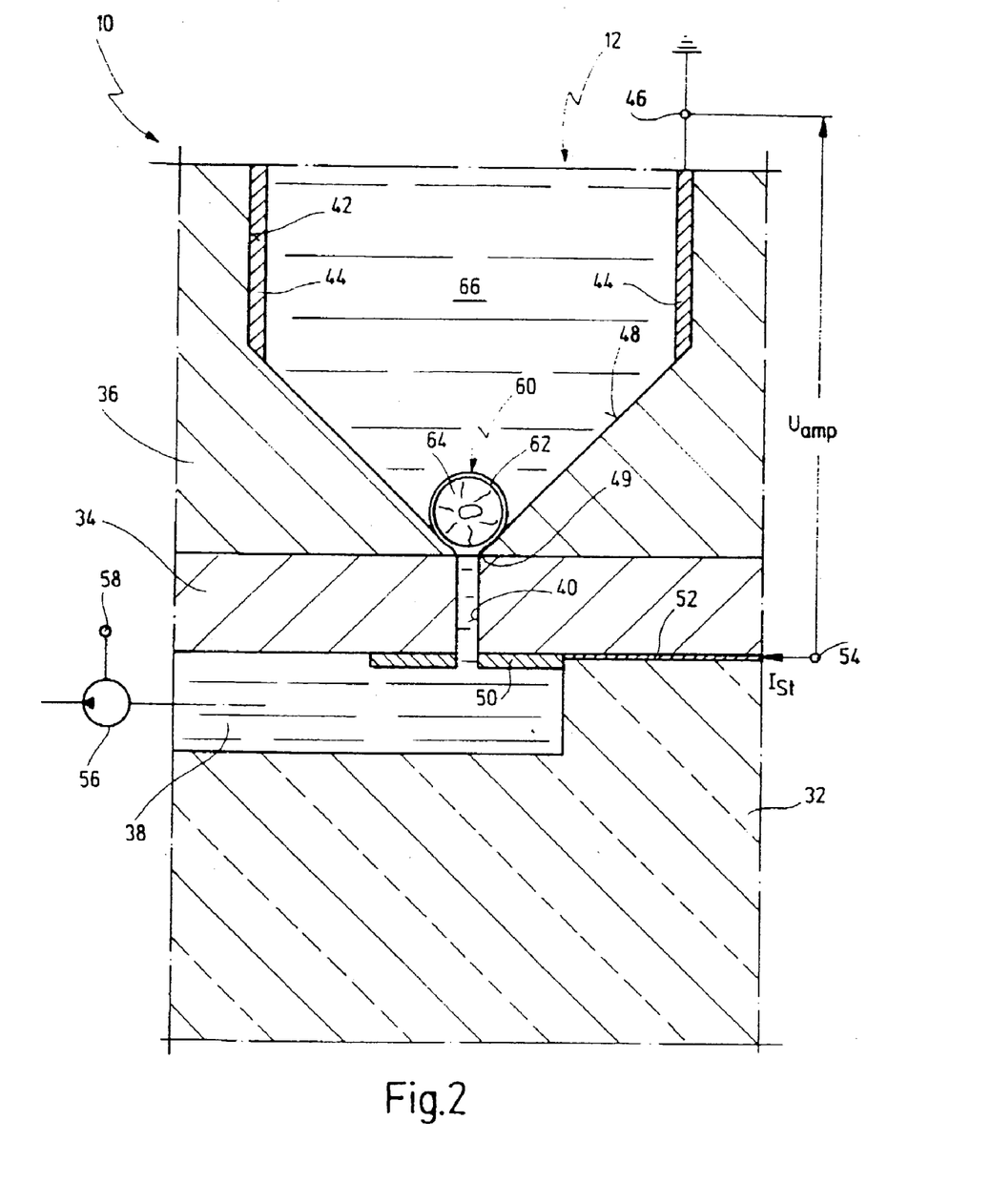
FIG. 2 shows a section through a micro-cuvette of the arrangement according to FIG. 1, likewise highly schematic.

As can be seen from FIG. 2, the plate 10 essentially consists of three layers. Located on the bottom layer 32 is a middle layer or a substrate 34 which is in the form of a sheet. A top layer 36 is fashioned as a micropatterned layer. The bottom layer 32 in this arrangement is preferably made of glass. The substrate 34 is preferably a polyimide sheet. The micropatterned layer 36 in contrast is preferably made of polymethyl methacrylate (PMMA).

Formed in the top side of the bottom layer 32 is a connecting channel 38. The connecting channel 38 is used for individually driving the micro-cuvette 12 shown in FIG. 2. The connecting channel 38 communicates via a vertical channel 40 in the substrate 34 with an opening 49 at the bottom 48 of the micro-cuvette 12. At its top, the micro-cuvette 12 is provided with a cylindrical section 42 which is lined with a reference electrode 44. The reference electrode 44 is connected to a first electric terminal 46. The latter is preferably connected to earth.

Adjoining the cylindrical section 42 at the bottom is a funnel-shaped section which forms the bottom 48 in which the opening 49 is provided.

An electrode 50 is arranged approximately annularly around the bottom end of the vertical channel 40. To this end it is applied to the underside of the substrate 34. The electrode 50 is connected to a lead 52 which runs between bottom layer 32 and the substrate 34. The lead 52 can e.g. together with the electrode 50 be printed, vapour-deposited, deposited or the like onto the underside of the substrate 34. The lead 52 is connected to a second electric terminal 54.

The electrodes 46 and 50 consist of silver/silver chloride (Ag/AgCl). Electrodes of this type are referred to in the art as "reversible" or as "non-polarizable". They offer the advantage of permitting not only a.c. voltage measurements on the cells, i.e. measurements of the potential spikes, but also d.c. voltage measurements. They can also be used for current injection.

Between the electrode 46 and 50 the measured voltage $U_{amp}$ is measured. In addition, a stimulation current $I_{st}$ can be fed in via the second terminal 54 parallel to the voltage measurement. This will be explained below in more detail with reference to FIG. 4.

Figure 3:
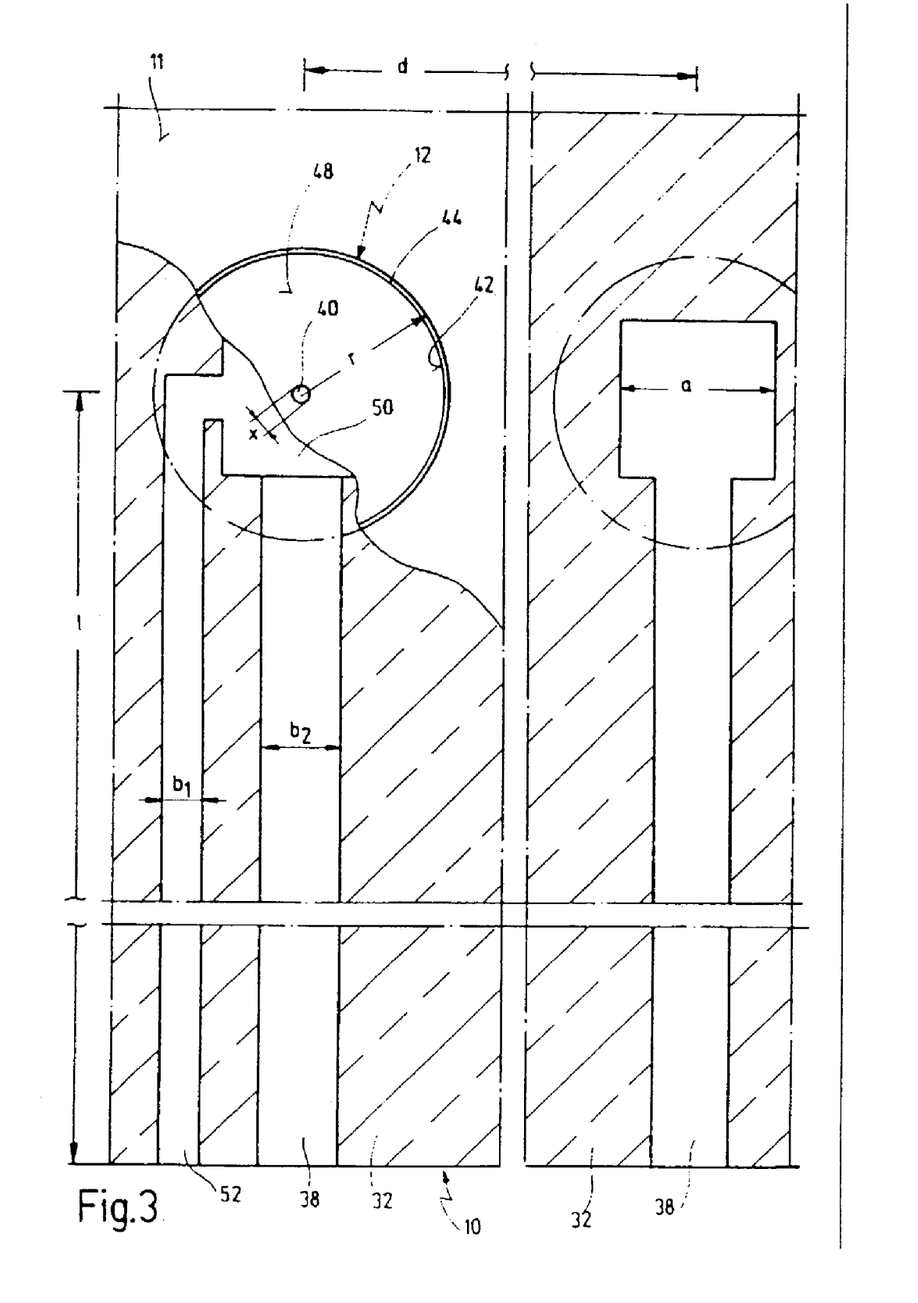
FIG. 3 shows a plan view from above of the micro-cuvette according to FIG. 2, on a slightly reduced scale.

As can be seen in the plan view from above according to FIG. 3, a plurality of micro-cuvettes 12 are arranged in the plate 10 in the form of a grid, the grid spacing spacing d being between 0.1 and 10 mm, preferably about 9 mm.

The micro-cuvettes 12 in the region of their cylindrical section 42 have an internal radius r of between about 1 and 9 mm, preferably about 7 mm, thus facilitating charging. The inner width x of the vertical channel 40 is less than 10 $\mu$m, preferably less than 5 $\mu$m.

The connector tracks 52 have a width $b_1$ of between 5 $\mu$m and 30 $\mu$m, preferably about 10 $\mu$m. The electrodes 50 are preferably of square design, in a plan view from above, and have an edge length a of between 20 $\mu$m and 60 $\mu$m, preferably about 40 $\mu$m. The connecting channels 38 have a width $b_2$ of between 10 $\mu$m and 40 $\mu$m, preferably about 20 $\mu$m.

The substrate 34 or the film has a thickness of between 2 $\mu$m and 40 $\mu$m, preferably about 5 $\mu$m.

The distance 1 of the micro-cuvettes 12 from the edge of the plate 10 is preferably at least 2 cm, thus achieving a high shunt resistance, i.e. electrical decoupling of the individual electrodes.

The electrode 50 and the connector tracks 52 are preferably made of gold.

FIG. 2 also illustrates that a micropump 56 can be integrated in the connecting channel 38, said micropump being drivable by means of a third terminal 58. Using the micropump 56 or using a central negative-pressure source, optionally with the incorporation of valves in the connecting channels 38, it is possible to establish a negative pressure, whose variation of the time can be controlled, in the connecting channels 38.

Figure 4:
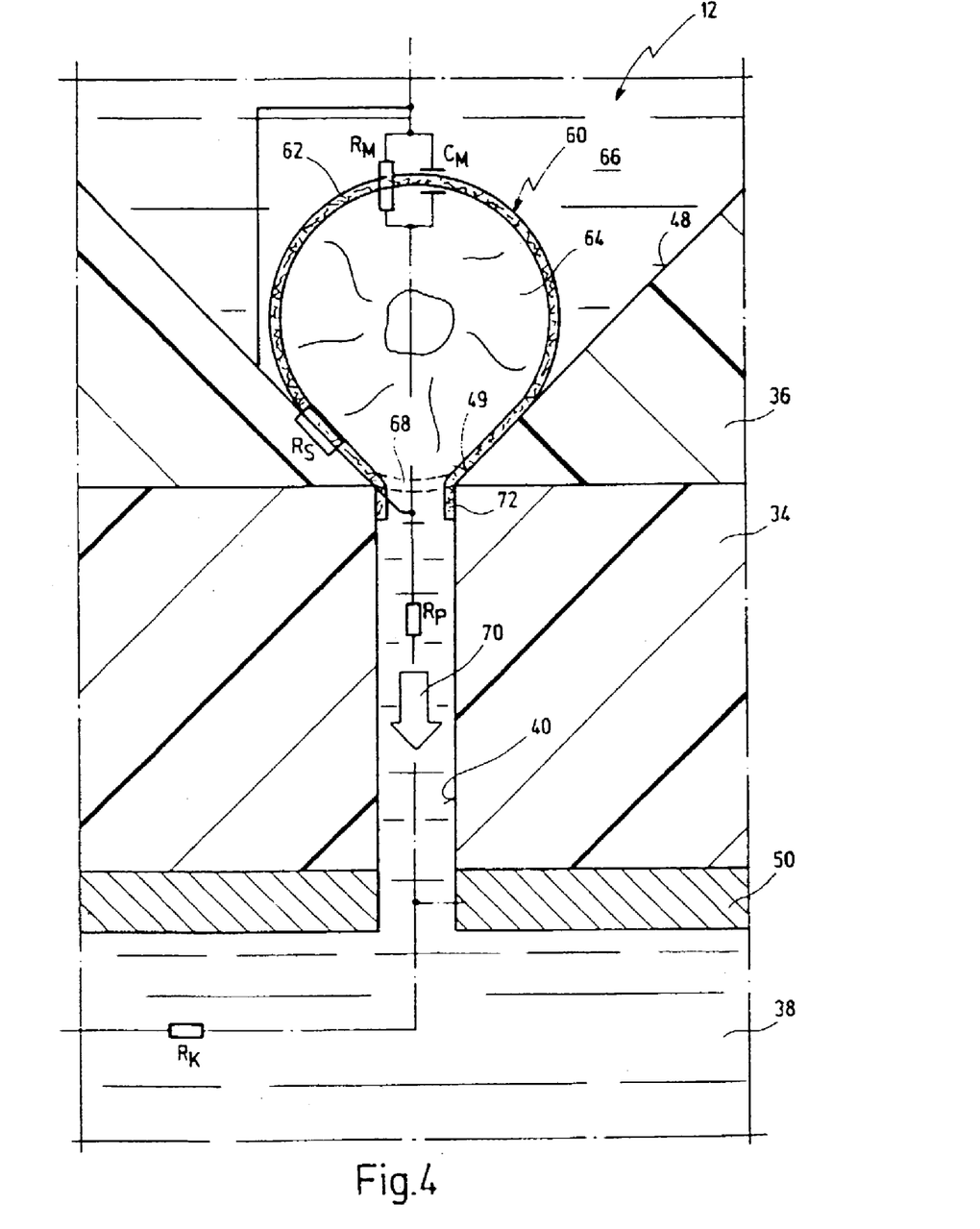
FIG. 4 shows a detail from FIG. 2 on an even larger scale, to illustrate the method according to the invention.

FIG. 4 shows, on an even larger scale, the situation where a cell 60 has sunk to the bottom 48 of the micro-cuvette 12. This is achieved either by gravity or controllably by the cell 60 being aspirated in a controlled manner by a preferably constant negative pressure being applied in the channel 40. The funnel-like shape of the section at the bottom 48 of the micro-cuvette 12 additionally causes the cells to be singled, so that as a rule only a single cell 60 will come to lie on the opening 49 at the bottom 48 of the micro-cuvette 12 above the channel 40.

In FIG. 4, the outer skin or membrane of the cell 60 is denoted by 62 and the cell interior by 64. The cell 60 is located in an ambient fluid 66 which, in the specific example shown, can also fill the connecting channels 38 and the channels 40 and can be replaced there. It lies on the bottom 49, on its underside 68.

As soon as this position is reached, a negative-pressure pulse is generated in the connecting channel 38, as indicated in FIG. 4 by an arrow 70. This negative-pressure pulse 70 is of such magnitude that the underside 68 is ruptured and, in the manner of a collar 72, is drawn into the channel 40. The cell interior 64 then communicates directly with the channel 40 and the liquid present therein. Alternatively, a low-pressure pulse can be dispensed with and the underside of the membrane can be rendered permeable by the addition of pore-forming substances, e.g. nyastatin or amphotericin B, resulting in low-resistance access to the cell interior without larger molecules being able to diffuse therethrough.

FIG. 4 additionally shows the electric equivalent circuit diagram of the cell 60.

$R_M$ and $C_M$ denote the resistance and the capacitance of the membrane 62. $R_S$ is the seal resistance, i.e. the insulation resistance between cell interior 64 and extracellular medium 66 outside the cell 60. $R_P$ is the resistance between the cell interior 64 and the electrode 50, while $R_k$ is the resistance between electrode 50 and reference electrode 44.

As a result of the collar 72 being drawn into the channel 40 and lying against the wall 48, without however reaching the relatively remote electrode 50, the value of $R_S$ is very high ("gigaseal")

In the zero-current state, i.e. when no current flows via the terminal 54 and through the connecting channel 38, the voltage $U_{amp}$ corresponds to the membrane voltage $U_M$ obtaining at the cell membrane. If, on the other hand, a finite current is able to flow via the connecting channel, the following relationship applies:

$$U_{amp} = \frac{R_k}{R_k + R_p} U_M,$$

i.e. the membrane voltage $U_M$ is proportional to the voltage $U_{amp}$.

If a stimulation current $I_{ST}$ is fed to the second terminal 54, the following relationship holds for the membrane voltage $U_M$ in the steady state:

$$U_M = \frac{R_S \cdot R_M}{R_M + R_S} I_{ST},$$

if $R_k \gg R_p + R_S R_m/(R_S + R_m)$. This condition is met, according to the invention, by sufficiently long connecting channels having a small channel cross section.

Both hydraulic and electric contact is therefore made in the above-described manner with the cell 60 at the bottom 48 of the micro-cuvette 12, by causing the required negative pressure via the electrolyte solution and—by the additional generation of a low-pressure pulse 70—bringing about the opening-up operation on the cell 60.

COMPARATIVE EXAMPLE

Figure 5:
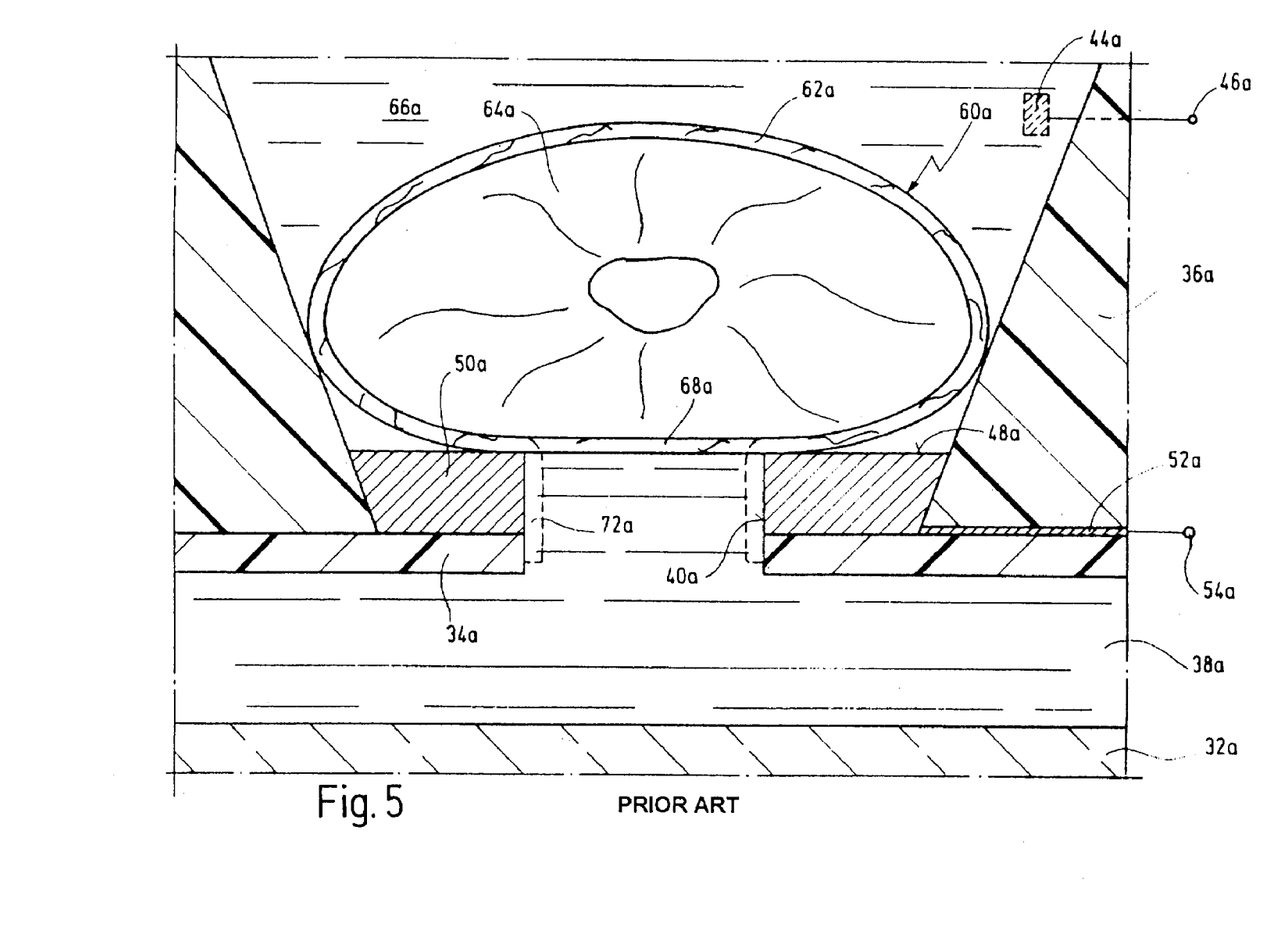
FIG. 5 shows a depiction, similar to FIG. 3, depicting the prior art.

To illustrate the difference between the procedure according to the invention and the prior art according to DE 197 12 309 A1, FIG. 5 shows a depiction which is similar to FIG. 4 and corresponds to the known arrangement, identical elements being indicated by identical reference symbols, with the addition of an "a" in each case.

As can be clearly gathered from FIG. 5, in this prior art the cell 60a lies directly on the electrode 50a. Electrical input to the cell 60a therefore takes place from outside, i.e. from the exterior of the membrane 62a. The channel 40a in this prior art is used solely to attract the cell 60a to the bottom 48a, by application of a specific, slight negative pressure, and to locate it fixedly there, the bottom 48a in this prior art, in contrast to the present invention, being formed by the electrode 50a.

Even if, in this prior art, a negative-pressure pulse were to be applied to the cell 60a via the channel 40a and the membrane 62a were to be opened up (of which there is no mention in said prior art), a collar 72a on the underside 68a of the cell 60a would form which covers the electrode 50a in the region of the channel 40a. Despite the cell 60a having been opened up, the electrode 50a would therefore still not permit a direct measurement through the cell interior 64a, but continue to lie only against the outside of the membrane 62a. With this prior-art device, the measurements, even with the underside 68a of the cell 60a having been opened up, would take a course no different from that described for the case where the negative pressure does not result in the cell 60a being opened up.

EXAMPLE 2

Figure 6:
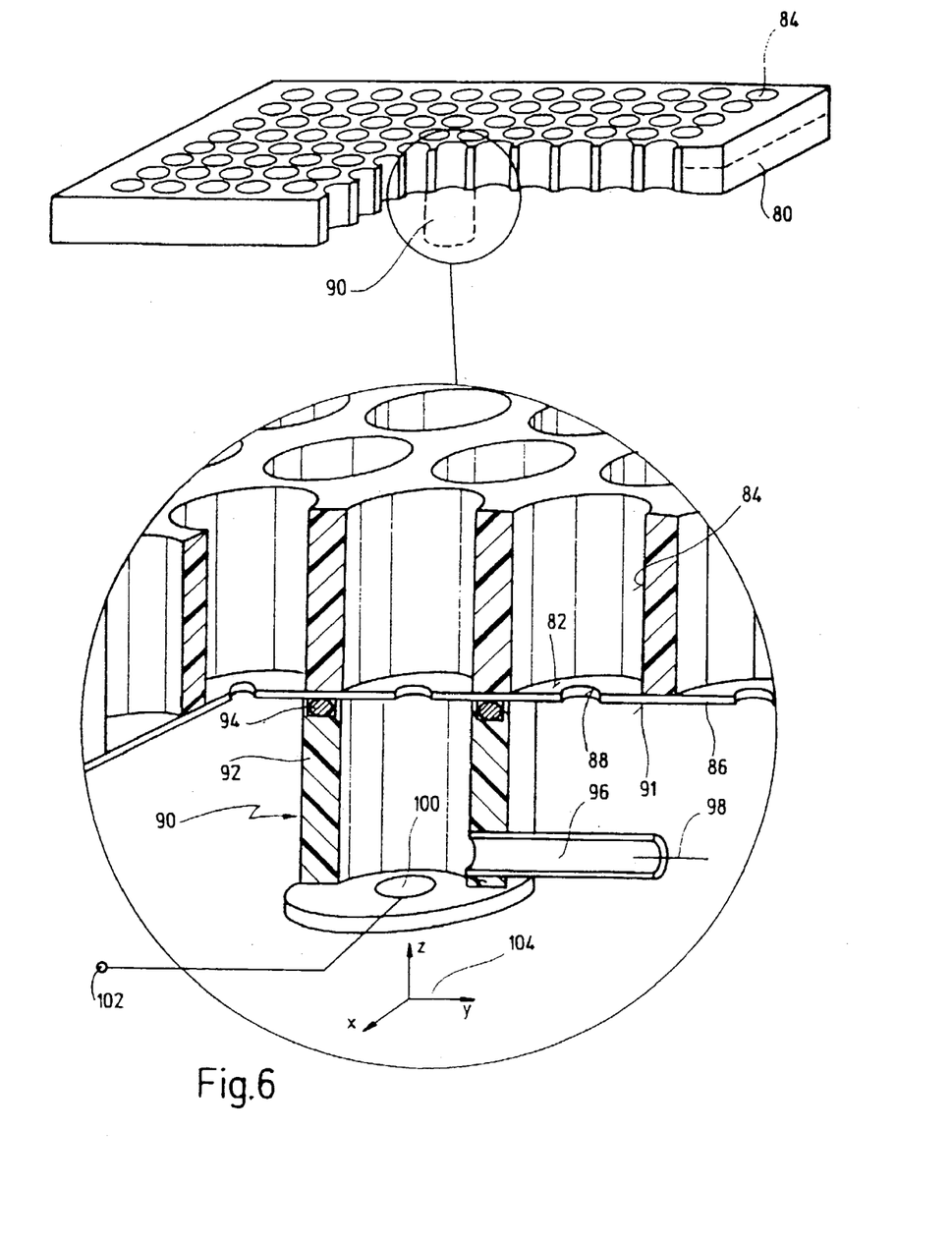
FIG. 6 shows a perspective view and an enlarged detail therefrom of a further specific embodiment of a device according to the invention.

Finally, FIG. 6 shows yet another specific embodiment of a device according to the invention.

In FIG. 6, 80 denotes a plate of a design which is conventional per se. Plates 80 of this type are referred to as a "96-well plate". They contain 96 vertical cylindrical drilled holes 84 arranged in a grid. These drilled holes 84 can be used as micro-cuvettes. As indicated in FIG. 6 top right by a dashed line, the plate 80 can alternatively be of multilayer, especially double-layer, design.

A bottom 82 of the cylindrical drilled holes or micro-cuvettes 84 is formed by a substrate 86 in the form of a sheet which is glued, welded or bonded in some other way to the underside of plate 80. The substrate 86 in each instance in the centre of the bottom 82 has a channel 88 in the form of a hole.

In contrast to the inventive exemplary embodiment according to FIGS. 2 to 4, no support having a system of connecting channels is present underneath the substrate 86. Instead a traversable hydraulic and measuring unit 90 is provided which can be individually moved up from below to the underside 91 of the sheet 86.

The unit 90 comprises a barrel-shaped chamber 92 which at its upper end face is provided with a ring seal 94. Thus the chamber 92 can be docked tightly to the underside 91 in such a way that the vertical axis of the chamber 92 is aligned with the axis of one hole 88 at a time.

Leading from the chamber 92 is a conduit 96 to a negative-pressure unit (not shown). Thus a negative-pressure pulse can be generated in the chamber 92, as indicated by an arrow 98.

Disposed on the bottom of the chamber 92 is an electrode 100 which is connected to an external terminal 102.

104 indicates a multiaxial traversing unit. The traversing unit 104 enables the hydraulic and measuring unit 90 to be guided along the underside 91, specifically from micro-cuvette 84 to micro-cuvette 84, and then to press the unit 90 tightly from below against the underside 91 around the respective hole 88 in question. By applying a negative-pressure pulse 98 to the conduit 96 it is then possible to carry out the same experiment as was explained hereinabove with reference to FIG. 4 relating to the first specific embodiment of the invention.

The first exemplary embodiment of the invention according to FIGS. 2 to 4 has the advantage that a compact plate comprising all the connecting channels for driving the micro-cuvettes 12 is available so that a plurality of measurements can be carried out sequentially or in multiplex mode without any further actuation devices, solely by driving valves, contacts and the like.

The second exemplary embodiment according to FIG. 6, in contrast, has the advantage that a commercially available plate can be used and that the expense for a bottom layer with a plurality of connecting channels, connector tracks and individual electrodes can be dispensed with.

EXAMPLE 3

Figure 7:
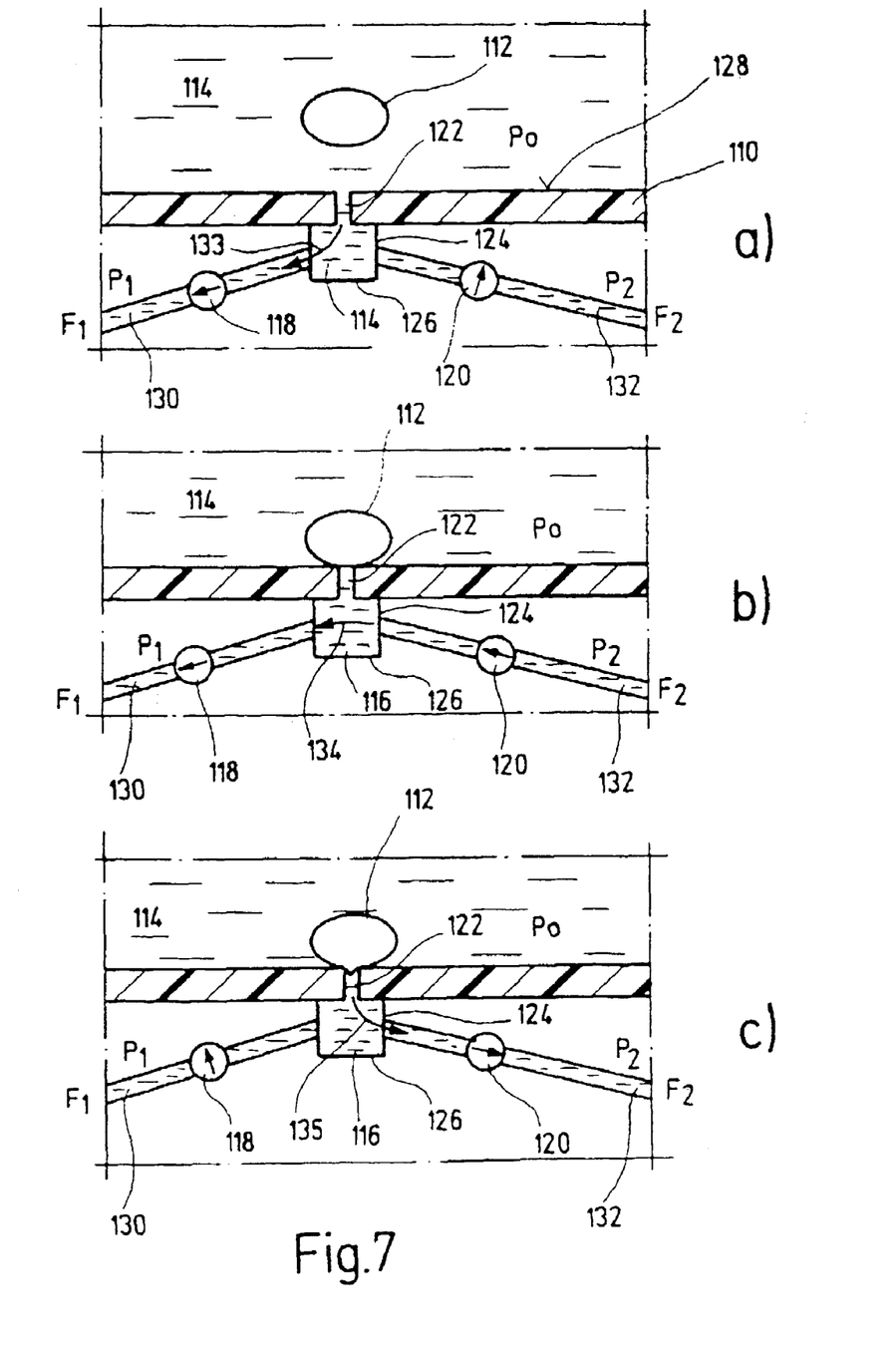

FIGS. 7a) to c) provide an extremely schematic depiction of a further exemplary embodiment of the invention, which is explained below in more detail.

Again, a substrate 110 is provided which, for example, can consist of a polyimide sheet. Formed in the substrate 110 is a plurality of channels, one of which, denoted by the numeral 122, is shown. Above the substrate 110 there is fluid in which cells 112 are present. Below the channel 122 a chamber 124 is formed which communicates with the channel 122, and at the bottom of which, in an arrangement similar to that of the embodiment according to FIG. 6, an electrode 126 is provided.

In contrast to the above-described embodiments, this chamber 124, however, communicates not with just one connecting channel but with two connecting channels 130, 132. These connecting channels 130, 132 can be connected, via valves 118, 120, to fluid reservoirs $F_1$ and $F_2$.

It goes without saying that the depiction is purely schematic and that the connecting channels 130, 132 can be formed e.g. in a photopolymerizable layer and that the valves are preferably configured at the outer ends of the channels.

If, as shown in FIG. 7a), the valve 120 is in a closed position and the valve 118 is in an open position, the application of a pressure $P_1$ to the channel 130 which is lower than the pressure $P_0$ in the fluid 114 results in a flow being established in the direction of the arrow 133 through the channel 122 and the feeder channel 130. This results in the cell 112 being aspirated and settling onto the surface 128 of the substrate 110 above the orifice of the channel 122 and forming a gigaseal if the negative pressure is maintained, so that the cell-attached configuration is established.

If then, in accordance with FIG. 7b), the valve 120 is opened, while the relationship $P_1<P_2<P_0$ is adhered to, the chamber 124 fills with intracellular medium from the fluid reservoir $F_2$, whilst a flow is established in the direction of the arrow 134 from the connecting channel 132 through the chamber 124 into the feeder channel 130. In this situation the pressure $P_2$ must be greater than the pressure $P_1$ for the flow to be directed in the direction of the arrow 134 from the connecting channel 132 to the connecting channel 130; in addition, the two pressures $P_1$ and $P_2$ must be lower than the pressure $P_0$ in the extracellular medium 114 by which the cell 112 is surrounded.

Then, in the following phase in accordance with FIG. 7c), the valve 118 is closed and a pulse-type negative pressure is applied to the connecting channel 132, so that P2 becomes very much smaller than $P_0$ ($P_2 << P_0$). This causes the underside of the membrane of the cell 112, the membrane patch, to be aspirated and, owing to the negative-pressure surges, to be ruptured, thereby establishing a whole-cell patch clamp. The flow during this phase is in the direction of the arrow 135 through the channel 122 and the connecting channel 132 towards the fluid reservoir $F_2$. A state is then reached in which the chamber 124 is filled solely with intracellular medium 116. Subsequently it is possible, via the valve 118, to work again with some other medium if this is desirable for the measurements to be carried out.

The advantage of this arrangement and this method is that it is possible to work with an accurately controlled intracellular medium, whose composition can be modified, or that it is even possible to use a different intracellular medium.

This embodiment comprising two or more connecting channels which can be controlled via valves can be combined, as a matter of principle, both with the embodiment previously explained with reference to FIGS. 1 to 4, and with the embodiment according to FIG. 6.

What is claimed is:

1. A device for carrying out electrical measurements on cells in a liquid environment, said device comprising a substrate having a surface and a plurality of first channels opening into said surface such that cells can be positioned above said first channels with an underside of their cell membranes on said surface, said device further comprising an aspirator channel for generating a pressure differential along said first channels, and comprising a reference electrode and a plurality of measuring electrodes for electrically scanning said cells, said plurality of measuring electrodes being arranged so as to be spaced apart from said reference electrode, wherein each measuring electrode is disposed at an end of an associated one of said first channels, said end facing away from said reference electrode, such that each measuring electrode is arranged spaced apart from a cell membrane of a cell that is positioned on the associated first channel.

2. A device for carrying out electrical measurements on cells located in a liquid environment, said arrangement comprising a substrate having a surface and at least one first channel opening into said surface, and an aspirator for generating a pressure differential along said first channel for aspirating said cells to said surface, said arrangement further comprising a first electrode and at least one second electrode for electrically scanning said cells, wherein said second electrode is arranged within the at least one first channel so as to be spaced apart, from said first electrode and from a cell membrane of a cell that is positioned on the first channel.

3. The device of claim 2, further comprising a controller for controlling said pressure differential, wherein the controller selectively induces the generation of a static pressure differential to establish a cell-attached configuration and of a pulse-type increase of said pressure differential for rupturing an underside of said cells.

4. The device of claim 2, wherein said first channel comprises a first end facing toward said cell and an opposite second end, said second electrode being disposed at said second end.

5. The device of claim 2, wherein said first channel comprises a first end facing toward said cell and an opposite second end, said second end being annularly surrounded by said second electrode.

6. The device of claim 2, wherein said first channel, at its end facing away from said first electrode, is connected via valves to a plurality of second channels via which a fluid can be supplied or discharged.

7. The device of claim 2, wherein a plurality of first channels is arranged in said substrate.

8. The device of claim 2, wherein at least one micro-cuvette having an opening at the bottom is disposed above said substrate.

9. The device of claim 8, wherein a plurality of micro-cuvettes are arranged in a plate.

10. The device of claim 9, wherein said plate has a multi-layer structure.

11. The device of claim 10, wherein said plate comprises a top layer, a middle layer and a bottom layer, said micro-cuvettes being disposed in said top layer, said middle layer forming said substrate in which said first channels are provided, and said bottom layer comprising connection channels connected to said first channels.

12. The device of claim 11, wherein said electrodes are disposed on an underside of said substrate or on a top side of said bottom layer.

13. The device of claim 11, further comprising conductor tracks leading to said electrodes and disposed between said substrate and said bottom layer.

14. The device of claim 11, wherein said top layer is comprised of polymethylmethacrylate (PMMA), and said bottom layer and said substrate are comprised of glass.

15. The device of claim 11, wherein said substrate has a layer thickness of between 2 $\mu$m and 40 $\mu$m.

16. The device of claim 11, wherein said substrate is comprised of a sheet in which a plurality of first channels is fashioned in the form of drilled holes.

17. The device of claim 16, wherein said substrate is disposed on an underside of a plate having a plurality of drilled holes defining micro-cuvettes having bottoms formed by said substrate.

18. The device of claim 16, wherein said substrate is disposed at an underside of a plate in which a plurality of drilled holes are fashioned as micro-cuvettes in whose bottom holes are provided by means of which said first channels of said substrate are centered in the bottoms of the micro-cuvettes.

19. The device of claim 2, wherein said substrate is connected to a bottom layer which comprises one or more layers of photopatternable materials which have connection channels running to said first channels.

20. The device of claim 19, wherein said bottom layer is arranged on to a glass mount.

21. The device of claim 2, further comprising a hydraulic and measuring unit having a chamber which is open toward an underside of said substrate and being positioned at said underside of said substrate in such a way that the chamber communicates with said at least first channel and is sealed with respect to the outside, said chamber containing at least one electrode which can be connected to at least one terminal channel which is connected to a negative-pressure source.

22. The device of claim 21, wherein said chamber is connected to a plurality of terminal channels via valves.

23. The device of claim 21, further comprising a multi-axial traversing unit for traversing and positioning said substrate and said hydraulic and measuring unit relative to one another.

24. The device of claim 15, wherein the substrate has a layer thickness of approximately 5 $\mu$m.

* * * * *

UNITED STATES PATENT AND TRADEMARK OFFICE
CERTIFICATE OF CORRECTION

PATENT NO. : 6,984,297 B2
APPLICATION NO. : 10/302163
DATED : January 10, 2006
INVENTOR(S) : Wilfried Nisch et al.

It is certified that error appears in the above-identified patent and that said Letters Patent is hereby corrected as shown below:

COLUMN 7

Line 2, delete "centred" and insert --centered--

Line 66, delete "FIG." and insert --FIGS.--

COLUMN 9

Line 2, delete "polymethyl methacrylate" and insert --polymethylmethacrylate--

Line 38, after "grid spacing" delete "spacing"

COLUMN 10

Line 40, after "("gigaseal")" insert --.--

COLUMN 12

Line 32, delete "c)" and insert -- 7c)--

COLUMN 13

Line 11, delete "P2" and insert --$P_2$--

Line 52, delete "arrangement" and insert --device--

Line 56, delete "arrangement" and insert --device--

UNITED STATES PATENT AND TRADEMARK OFFICE
CERTIFICATE OF CORRECTION

PATENT NO. : 6,984,297 B2
APPLICATION NO. : 10/302163
DATED : January 10, 2006
INVENTOR(S) : Wilfried Nisch et al.

It is certified that error appears in the above-identified patent and that said Letters Patent is hereby corrected as shown below:

COLUMN 14

Line 48, delete "Claim 16" and insert --Claim 17--

Line 51, after "which" delete "said first"

Line 52, after "channels" delete "of"

Signed and Sealed this

Twentieth Day of February, 2007

JON W. DUDAS
*Director of the United States Patent and Trademark Office*